United States Patent [19]

Cline et al.

[11] Patent Number: 4,919,655
[45] Date of Patent: Apr. 24, 1990

[54] SINGLE USE SYRINGE

[76] Inventors: Jack B. Cline, 12827 Bromwich St., Arleta, Calif. 91331; Stephen W. Ammerman, 619 Resolano, Pacific Palisades, Calif. 90272

[21] Appl. No.: 221,220

[22] Filed: Jul. 19, 1988

[51] Int. Cl.⁵ .............................................. A61M 5/00
[52] U.S. Cl. .................................................. 604/110
[58] Field of Search .............. 604/110, 190, 236, 237, 604/247, 248, 249

[56] References Cited

U.S. PATENT DOCUMENTS 4,781,683  11/1988  Wozniak et al. ................... 604/110

Primary Examiner—John D. Yasko
Attorney, Agent, or Firm—Jack C. Munro

[57] ABSTRACT

A syringe for the injecting of medicines into the human body wherein the syringe includes a valve system which permits the syringe to only be used once.

16 Claims, 13 Drawing Sheets

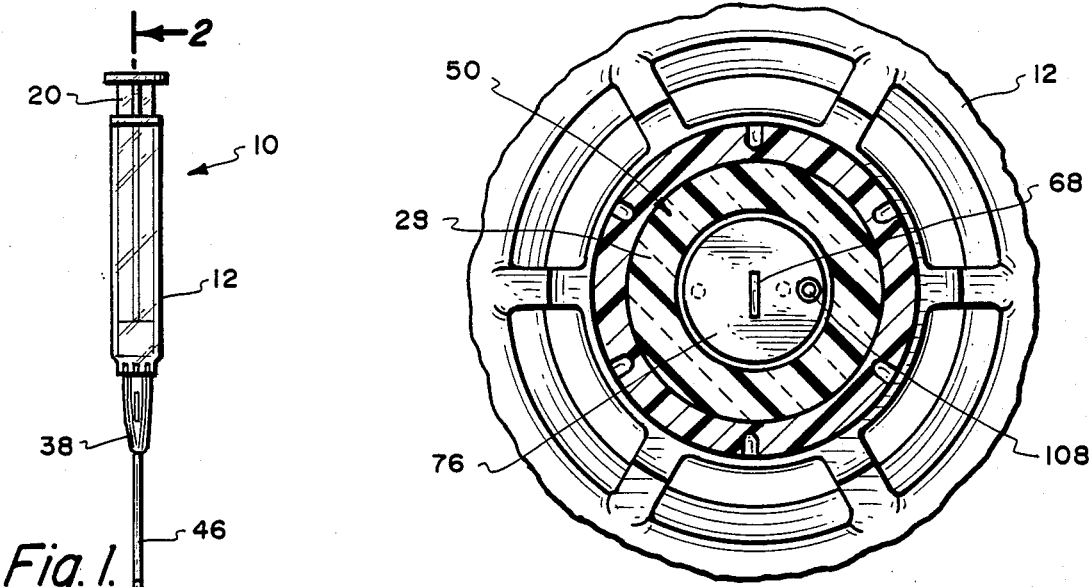
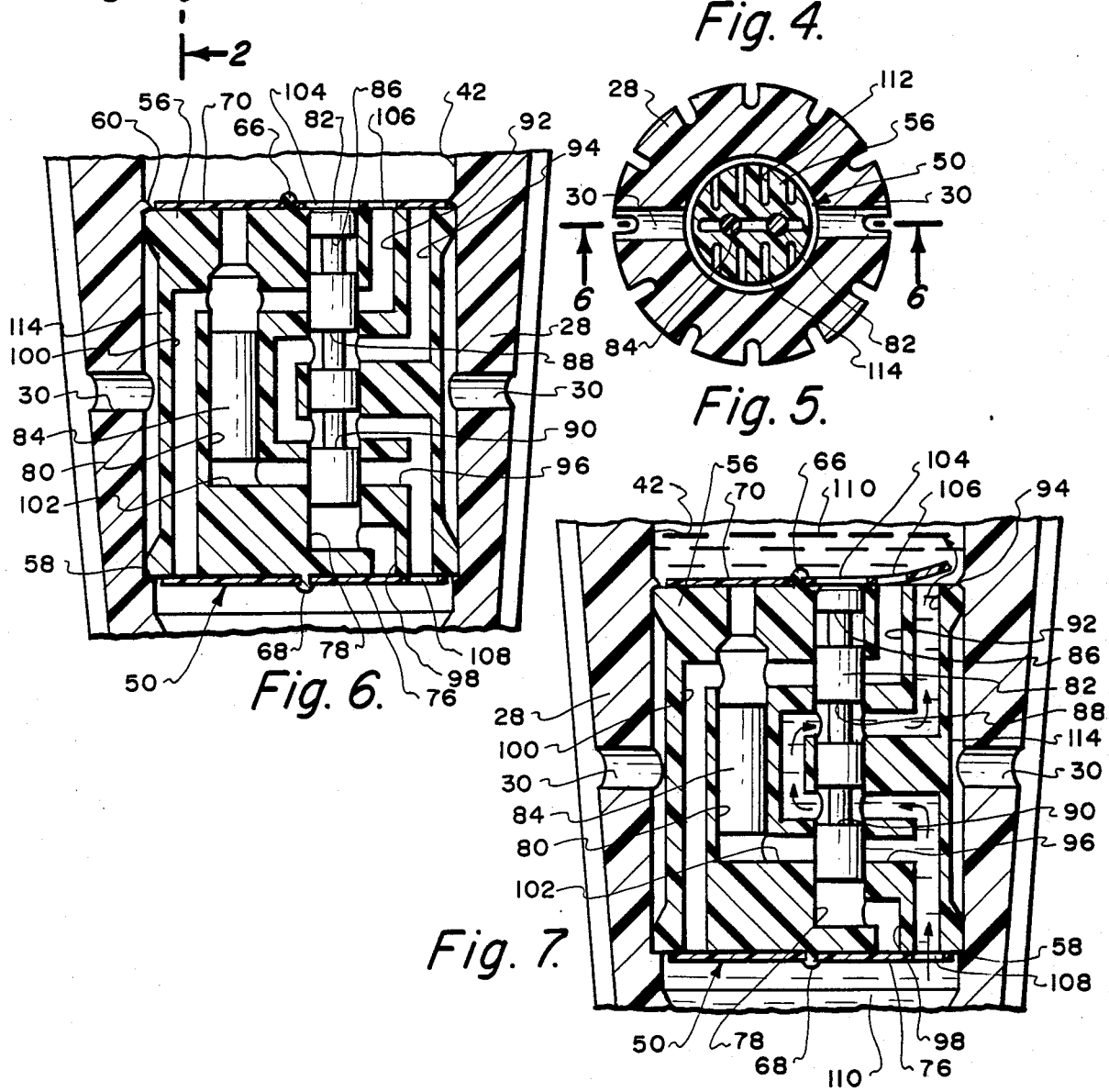

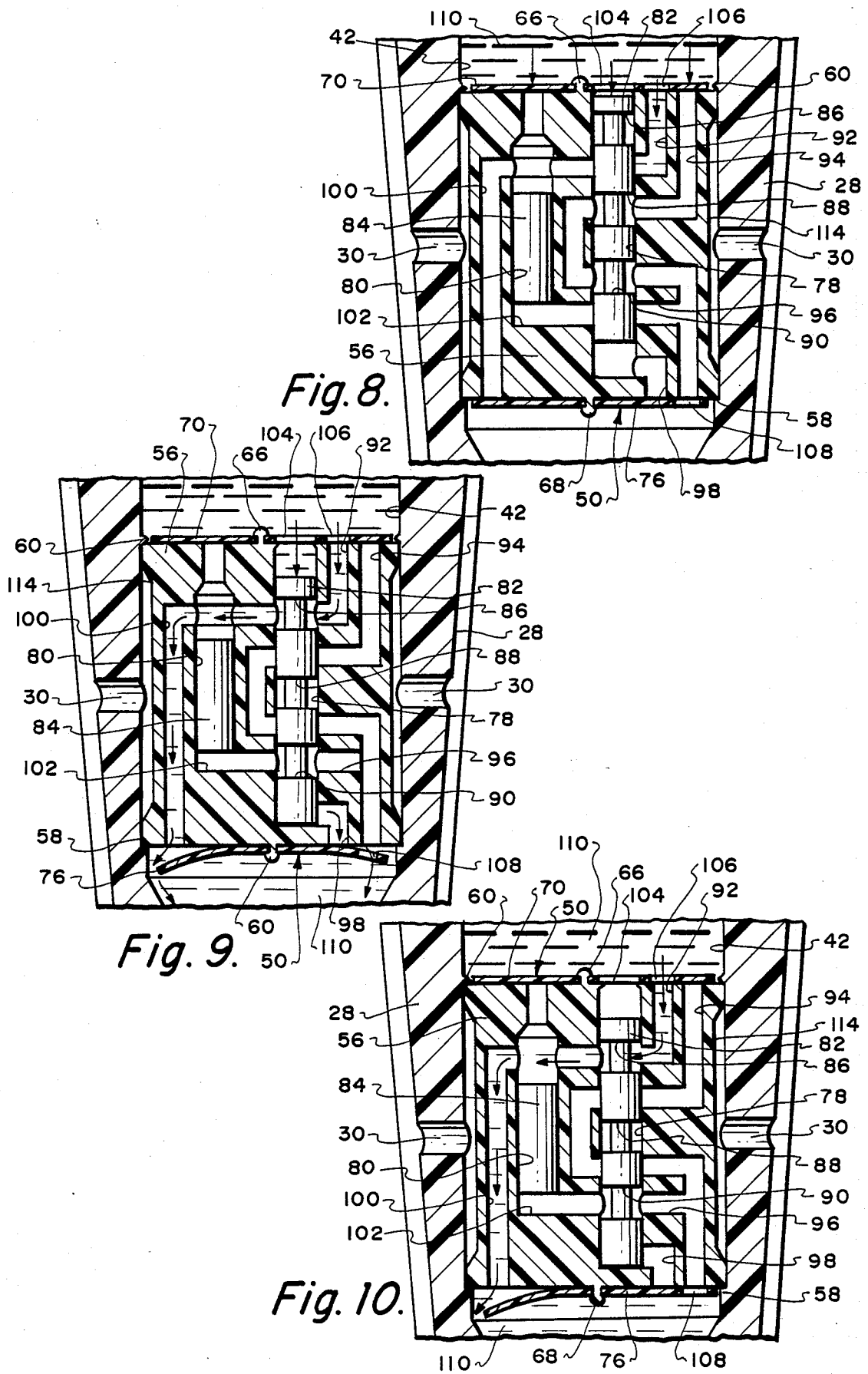

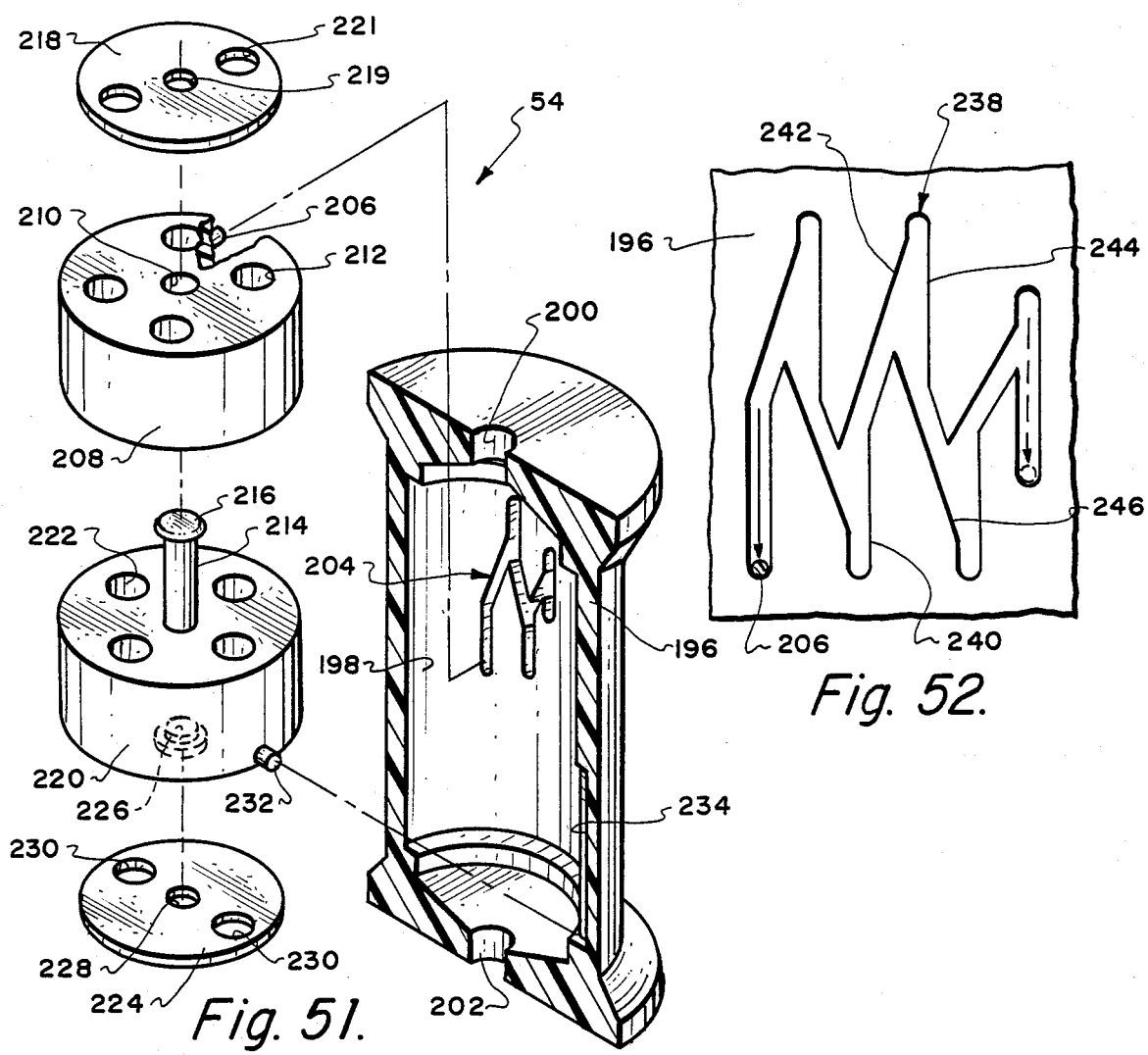
Fig. 51.
Fig. 52.
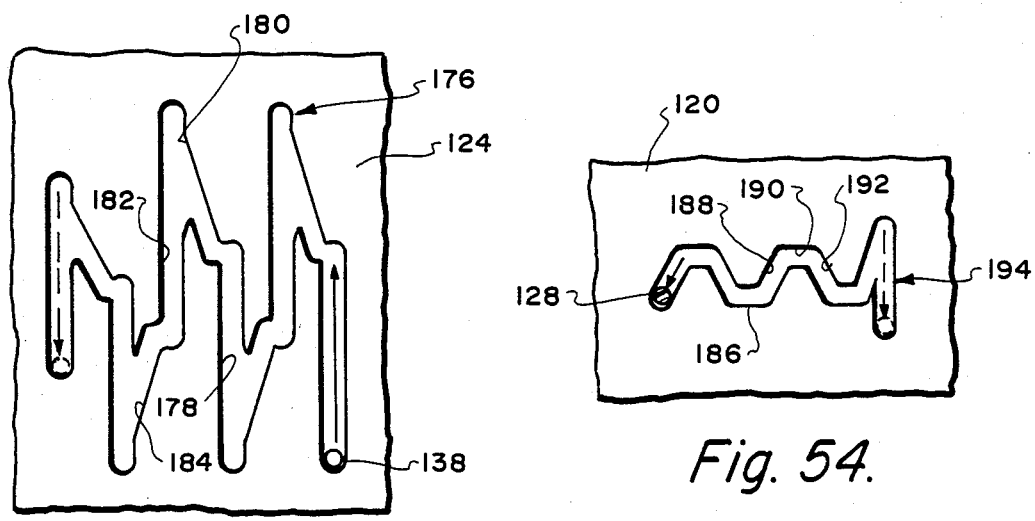
Fig. 53.
Fig. 54.

4,919,655

SINGLE USE SYRINGE

BACKGROUND OF THE INVENTION

The field of this invention relates to medical equipment and more particularly to a new and novel syringe for the injecting of medicines into the body of human beings.

Syringes have long been utilized in the medical profession for injecting patients with drugs. These drugs are administered at the direction of a skilled medical practitioner.

However, within the present day society, there is substantial usage of illegal drugs. Some of these illegal drugs require the use of a syringe. It is common for drug addicts to constantly reuse a syringe other than using a new syringe for each injection. Also, it is common that drug addicts transfer their syringes from one addict to another.

It is well known that any infections can be transferred from one person to another by using of an unclean syringe. A disease that is most commonly transferred in this manner is Aids and at the present time there is no known cure.

As far as this invention is concerned, the syringe includes the needle.

SUMMARY OF THE INVENTION

The primary objective of the present invention is to construct a syringe that cannot be used more than once, therefore, eliminating any possibility of transfer of the syringe from one party to another and hence the transfer of any infectious disease such as Aids.

Another objective of the present invention is to construct a single use syringe which can be incorporated within conventional syringe construction minimizing the amount of change of the conventional syringe structure.

Another objective of the present invention is to construct a single use syringe which can be manufactured near the present manufacturing cost of syringes.

The structure of the present invention is designed to be incorporated within a conventional syringe. Conventional syringes are made to include a barrel within which the liquid that is to be injected is located. The barrel includes an outlet opening. Connecting with the side wall of this outlet opening is a hollow needle. The liquid is to be injected through this needle. The needle includes a sharp outer point which is to be used to penetrate the skin of a human being. Connected with the barrel is a plunger which is to be manually pushed to cause injecting of the liquid from the barrel through the needle and into the human being. A valve assembly is mounted in conjunction with the outlet opening of the barrel of the syringe and the inlet opening of the needle. This valve assembly permits movement of the plunger in an outward manner to load the syringe with the liquid. This valve assembly then permits the liquid to be injected into the patient. A modified form of the valve assembly will permit testing of the syringe to see that a vein or artery has been reached. At this time further use of the syringe is prevented.

BRIEF DESCRIPTION OF THE DRAWINGS

FIG. 1 is an overall side elevational view of a typical syringe within which has been incorporated the valve structure of the present invention;

FIG. 4 is a cross-sectional view taken along line 4—4 of FIG. 3;

FIG. 5 is a cross-sectional view through the first embodiment of valve utilized within the needle of FIG. 1 taken along line 5—5 of FIG. 3;

FIG. 6 is a cross-sectional view through the first embodiment of valve unit taken along line 6—6 of FIG. 5 showing the valve unit in the initial position as it would be received by the medical practitioner;

FIG. 7 is a view similar to FIG. 6 but showing the valve in the position of loading of the syringe with the liquid to be injected;

FIG. 8 is a view similar to FIG. 7 but showing the valve unit in the initiating of purging of air from the syringe;

FIG. 9 is a view similar to FIG. 8 but showing the valve unit in the purging position;

FIG. 10 is a view similar to FIG. 9 but showing the valve unit in the liquid injecting position;

FIG. 51 is an exploded view, partly in cross-section, of the third embodiment valve unit of this invention;

FIG. 52 is a modified form of a guide track which could be utilized instead of the guide track of FIG. 17 which would permit the valve units to move in the loading direction for the purpose of testing to insure that the needle of the syringe has been within a vein or artery and then permit the injection to occur if such location has been obtained and also showing the pin in conjunction with the guide track in its location corresponding to the position of the valve unit of FIG. 16;

FIG. 53 is a view similar to FIG. 52 but showing the location of the pin corresponding to the position in FIG. 28; and FIG. 54 is a view similar to FIG. 18 but of a modified form of guide track that would be utilized in conjunction with the guide track of FIG. 52.

DETAILED DESCRIPTION OF THE SHOWN EMBODIMENT

Figures 2, 3:
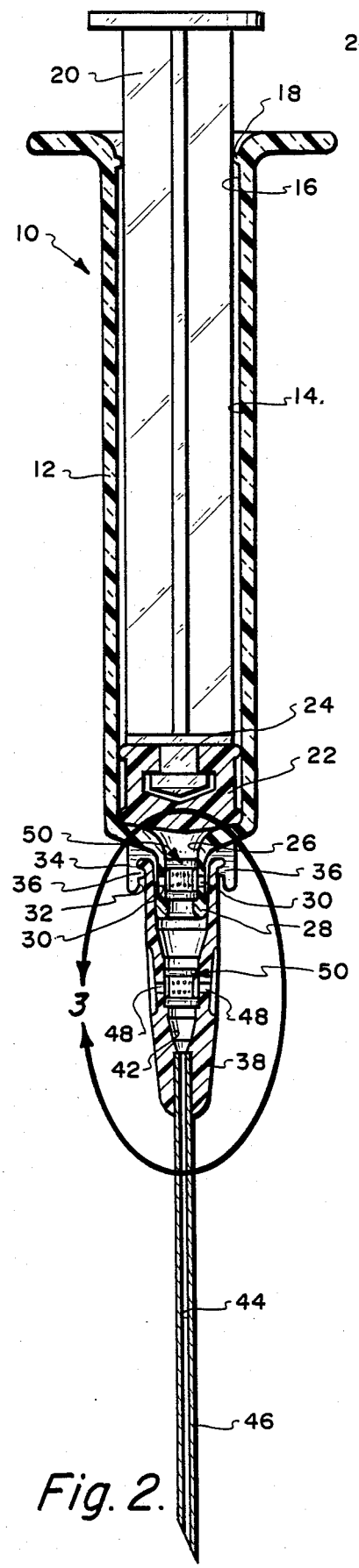
FIG. 2 is a cross-sectional view through the syringe taken along line 2—2 of FIG. 1.
FIG. 3 is an enlarged cross-sectional view of the valve structure incorporated within the syringe of the present invention taken along line 3—3 of FIG. 2.

Referring particularly to FIGS. 1, 2 and 3 of the drawings, there is shown a conventional syringe 10 which is constructed of a barrel 12 which has an elongated internal chamber 14. The liquid (not shown) that is to be injected is to be located within the internal chamber 14. One end of the internal chamber 14 is open defining an access opening 16. Within the confines of the access opening 16 is located an annular ridge 18. The annular ridge 18 functions as a "stop" preventing disengagement of a plunger 20 from within the internal chamber 14. The plunger 20 terminates in a flexible tip 22 which is mounted on enlarged head member 24 of the plunger 20. The flexible tip 22 forms a snug fit in conjunction with the wall of the internal chamber 14. However, movement of the tip 22 within the chamber 14 is permitted. The tip 22 is movable from the position shown in FIG. 2 to a completely withdrawn position which is abutting against the annular ridge 18.

The opposite end of the barrel 12 is necked down forming a narrow outlet opening 26. This outlet opening 26 is defined within annular extension 28 of the barrel 12. The annular extension 28 includes a plurality of holes 30 formed therein. The function of these holes 30 will be explained further on in this specification.

Surrounding circumferentially the annular extension 28 and forming an annular space 32 therebetween is an outer attaching sleeve 34. The attaching sleeve 34 is integral with the barrel 12. The attaching sleeve 34 includes a screw thread 36. The inner end of a needle housing 38 is to be locatable within the space 32. This inner end of the needle housing 38 defines an annular shoulder 40. It is this shoulder 40 that is captured by the thread 36 thereby securely retaining in place the needle housing 38 to the barrel 12. It is also to be understood that the needle housing 38 can be removed with a new needle housing being attached in connection with the barrel 12.

The needle housing 38 includes an interior chamber 42. The interior chamber 42 connects with passageway 44 of a needle 46. Within the needle housing 38 are located a series of holes 48 which connect the interior chamber 42 to the ambient. The purpose of the holes 48 will be explained further on in this specification.

Fixedly mounted to the wall of the chamber 26 is a valve unit 50. A similar valve unit 50 is fixedly mounted to the wall surface of the interior chamber 42. Each of the valve units 50 are identical and will be discussed in more detail in relation to FIGS. 4 through 14. It is normally desirable to include a valve unit 50 in conjunction with the barrel 12 and a separate valve unit 50 in conjunction with the needle housing 38. However, in some instances, only a single valve unit may be utilized. In one particular instance, if per chance the needle housing 38 is permanently fixed to the barrel 12, there will be utilized only a single valve unit such as within the chamber 26 or within the chamber 42.

The valve unit 50 is what is deemed to be the first embodiment of this invention. However, there is a second embodiment 52 of valve unit which is shown in FIGS. 15 through 31. This second embodiment 52 could be utilized in place of the first embodiment 50. Still further, there is a third embodiment 54 of this invention which could be utilized in place of the embodiment 50.

Embodiment 50 has a valve body 56 (FIG. 8). This valve body 56 is to be mounted against an annular shoulder 58 integrally formed to the wall of the interior chamber 42. The upper edge of the valve body 56 is held in place by an inwardly extending annular protuberance 60 which is integrally formed onto the wall of the interior chamber 42. The mounting of the valve unit 50 in conjunction with the chamber 26 is accomplished in the same manner through the use of a shoulder 62 and an annular inwardly extended ring 64. The valve body 56 will normally be injection molded of plastic.

The valve body 56 defines an upper surface which has a centrally located snap tab 66. A similar snap tab 68 is mounted in a protruding outward manner from the lower surface of the valve body 56. It may be that the tabs 66 and 68 will not be precisely centrally mounted on their respective surface so as to avoid interference with any working part of the valve body 56. Snap tab 66 is to connect with an opening 72 formed within a flexible flapper valve 70. In a similar manner, snap tab 68 is to pass through an opening 74 of a flexible flapper valve 76. The normal at-rest position for the flapper valves 70 and 76 is snugly abutting against their respective surfaces of the valve body 56.

Formed within the valve body 56 is a first spool chamber 78 and a second spool chamber 80. Mounted within the spool chamber 78 is a valve spool 82. A second valve spool 84 is movably mounted within the chamber 80. The valve spool 82 is basically cylindrical with the exception of decreased diameter sections 86, 88 and 90. The valve spool 84 is solidly cylindrical and of constant diameter.

Formed within the valve body 56 are passages 92, 94, 96 and 98 which connect with the valve spool chamber 78. Passage 92 also connects with spool chamber 80 through connecting passage 100. Also, between the chamber 80 and chamber 78 is a connecting passage 102 which is in alignment with the passage 96. The flapper valve 70 includes a hole 104 and a hole 106. The flapper valve 76 includes a hole 108.

The operation of the valve unit 50 is as follows: When the syringe 10 is received and is removed from its package, the plunger 20 is in the position shown in FIGS. 1 and 2 with the tip 22 being located directly adjacent the outlet opening 26. Each of the valve units 50 are in the position shown in FIG. 6. The user proceeds to insert needle 46 into a medicine container (not shown) and then proceeds to withdraw plunger 20 until the desired amount of medicine has been placed within the internal chamber 14. The maximum amount of medicine that could be contained within the chamber 14 is when the tip 2 is located directly adjacent the annular ridge 18. As medicine is being drawn into internal chamber 14, the medicinal liquid 110 is conducted through hole 108 into passage 94 past decreased diameter areas 90 and 88 and displacing a portion of the flapper valve 70 as the liquid fills the internal chamber 14 (FIG. 7). Once the desired amount of liquid 110 has been located within the internal chamber 14, the filling procedure is stopped by the plunger 20 no longer being moved. At that particular time, the flapper valve 70 will automatically return to be flush with the upper surface of the valve body 56 thereby closing passage 94.

By the applying of a small amount of pressure to the plunger 20 in a direction toward the outlet chamber 26, any air that is contained within the passages of the valve body 56 is to be removed. The fluid pressure is transmitted through hole 104 to valve spool 82 which results in the valve spool 82 being moved to a lower position blocking passage 94 and opening of passages 102, 96, 92 and 100 (FIG. 9). Continued slight movement of the plunger 20 results in air being discharged from passages 92, 98 and 100 past the flapper valve 76 and hence through the interior chamber 42 and passage 44 of the needle 46 into the ambient. Once this purging of air has occurred, injection of the medicinal liquid 110 can occur and this position is shown in FIG. 10.

Figure 11:
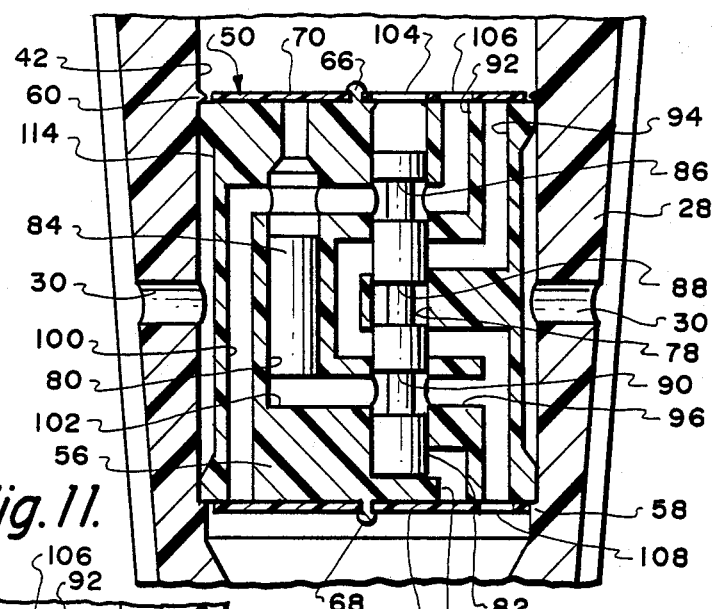
FIG. 11 is a view similar to FIG. 10 but showing the valve unit in the injection completion position.
Figure 12:
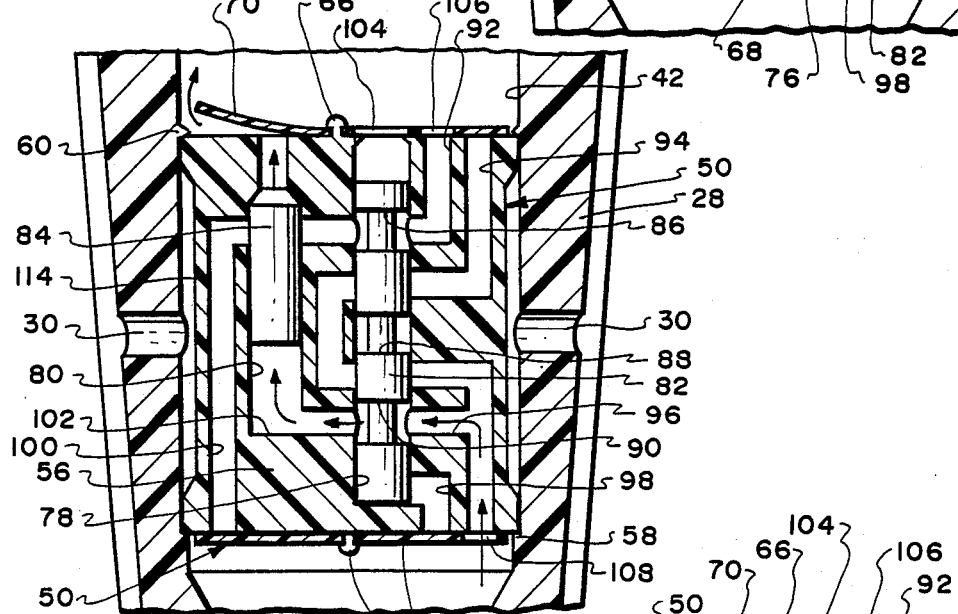
FIG. 12 is a view similar to FIG. 11 but showing the valve unit in an attempt to refill position.

This injection of medicinal liquid 10 occurs when the liquid 110 conducted through the passage 92 into passage 100 and past the flapper valve 76. As long as the plunger 20 is continued to move toward the outlet chamber 26, the medicinal liquid 110 will be continued to be conducted through the valve body 56. When the total amount of medicinal liquid 110 has been injected, the flapper valve 76 will return to its at-rest position such as shown in FIG. 11 of the drawings. At this particular time, the normal procedure would be to remove the syringe 10 from the patient and discard such as it cannot now be reused.

Figure 13:
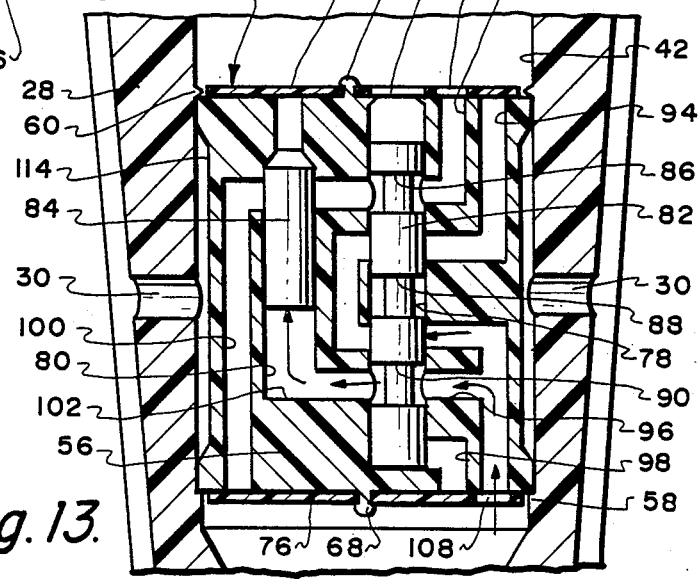
FIG. 13 is a view similar to FIG. 12 but showing the valve unit in the completely closed position which stops any further usage of the syringe.
Figure 14:
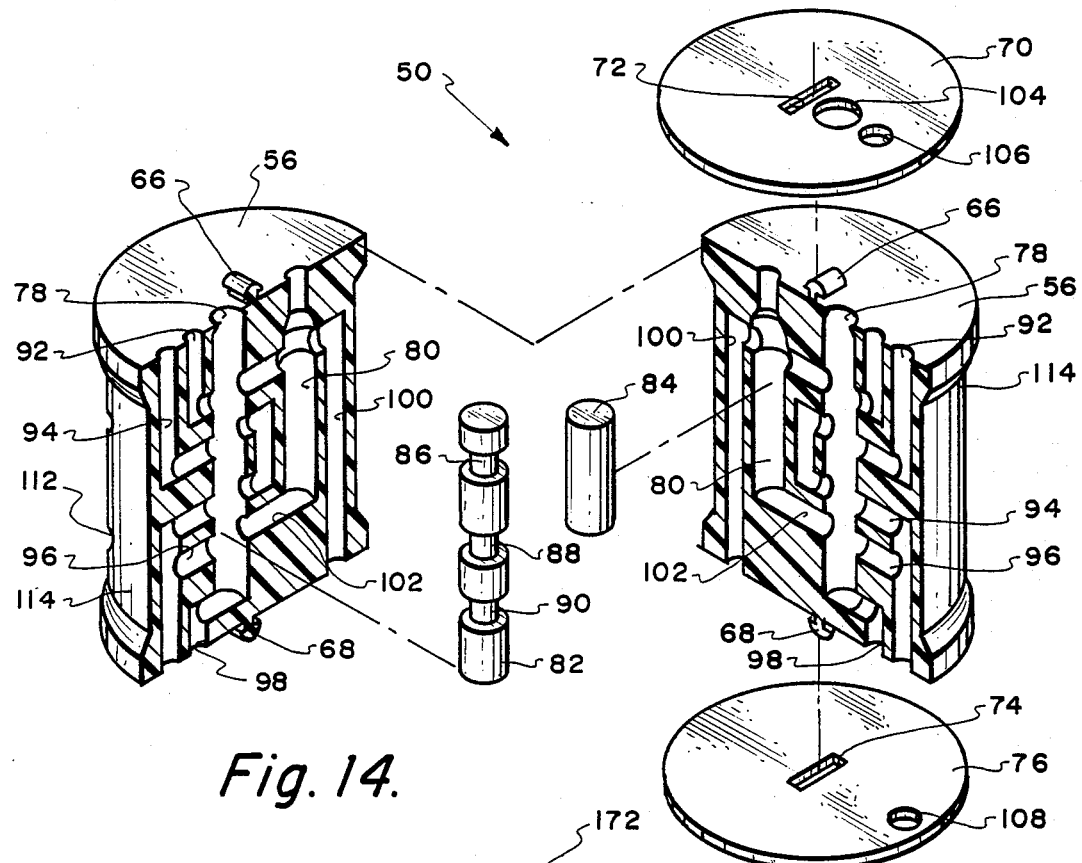
FIG. 14 is a cross-sectional exploded view of the first embodiment of valve unit.
Figure 15:
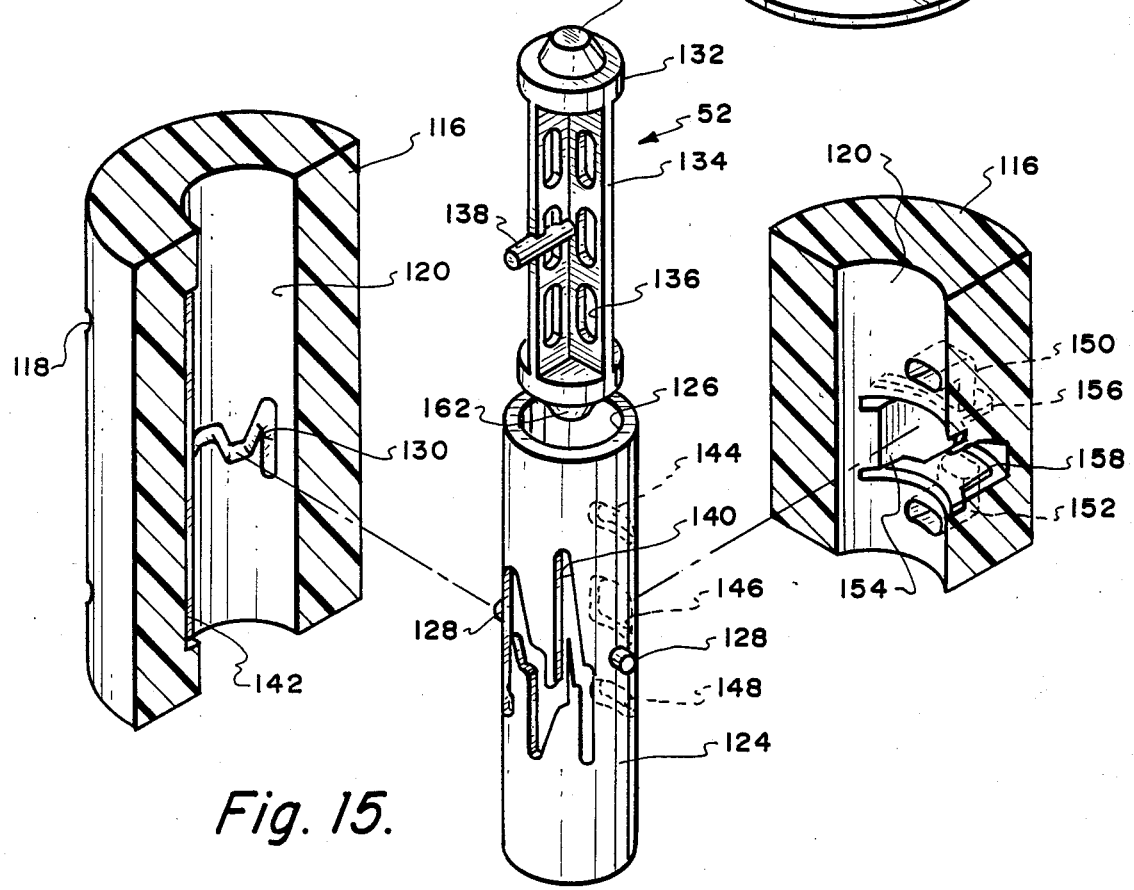
FIG. 15 is a cross-sectional exploded view of a second embodiment valve unit of this invention.
Figure 16:
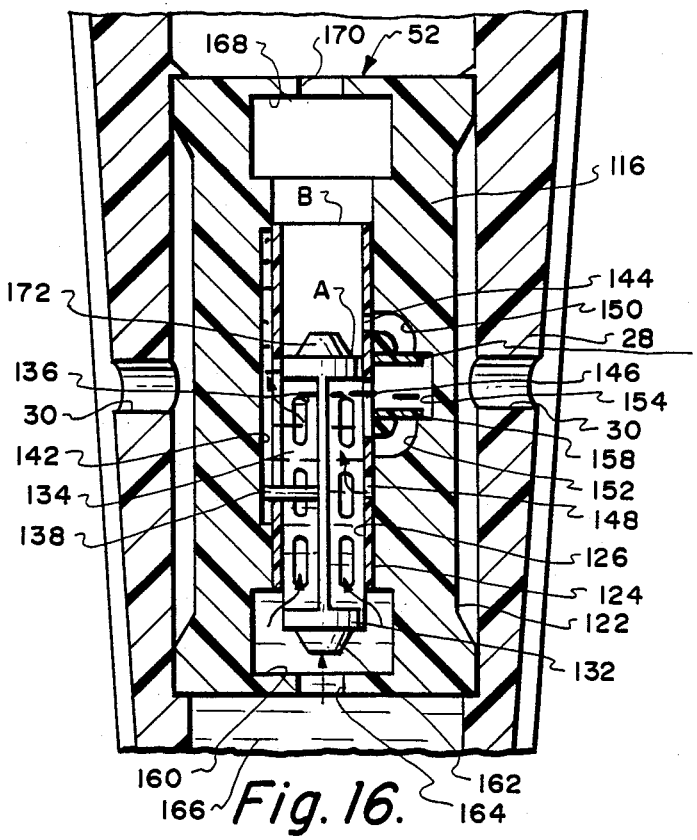
FIG. 16 is a longitudinal cross-sectional view of the second embodiment of valve unit of this invention showing the valve unit in the initial position as the medical practitioner receives it.
Figure 17:
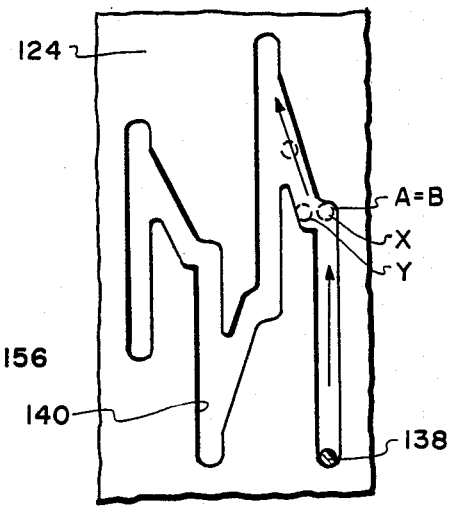
FIG. 17 is a depiction of a guide track which is utilized in conjunction with the valve unit of FIG. 16 showing the pin located within the guide track at the position corresponding to FIG. 16.
Figure 18:
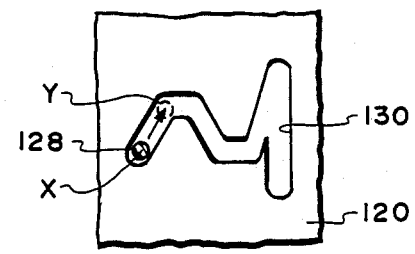
FIG. 18 is a depiction of a second guide track which is incorporated within the second embodiment of this invention showing a second pin in the position of this guide track corresponding to the position of FIG. 16.
Figure 19:
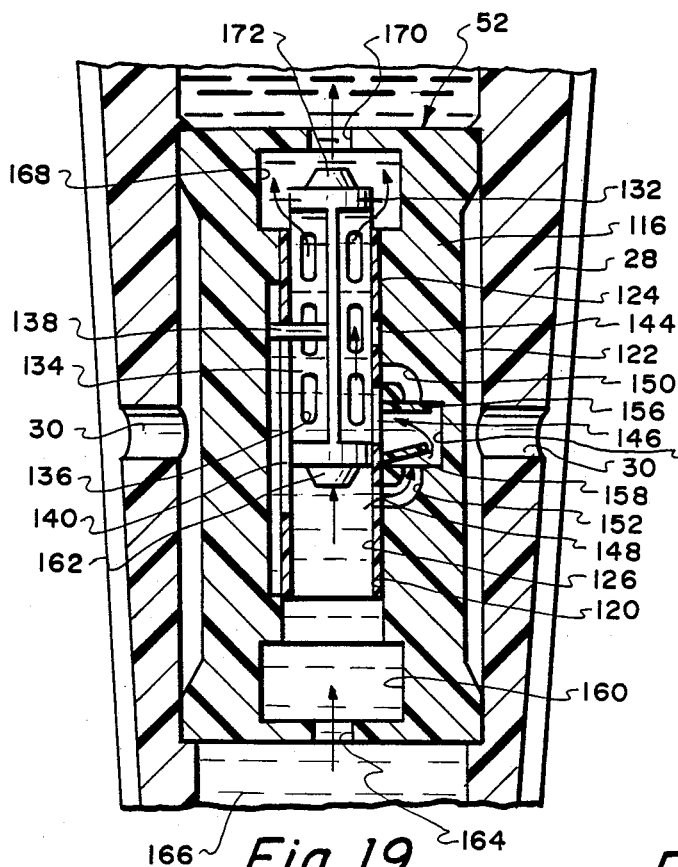
FIG. 19 is a view similar to FIG. 16 but showing the second embodiment of valve unit in the liquid filling position.
Figure 20:
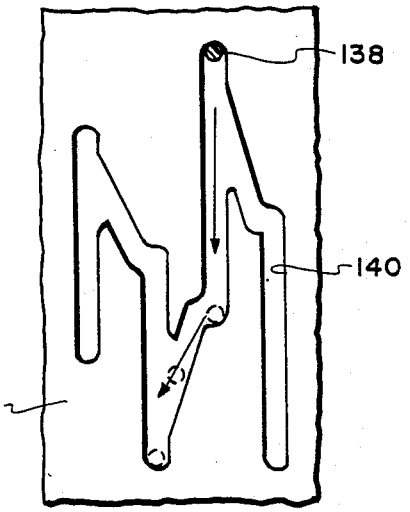
FIG. 20 is a view similar to FIG. 17 but showing the pin in the position corresponding to FIG. 19.
Figure 21:
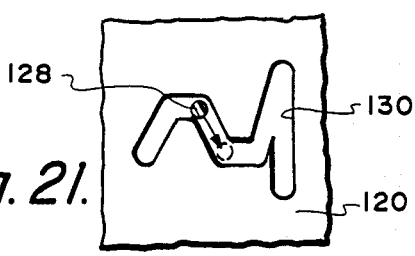
FIG. 21 is the second guide track and showing its pin in conjunction therewith again corresponding with the position of FIG. 19.
Figure 22:
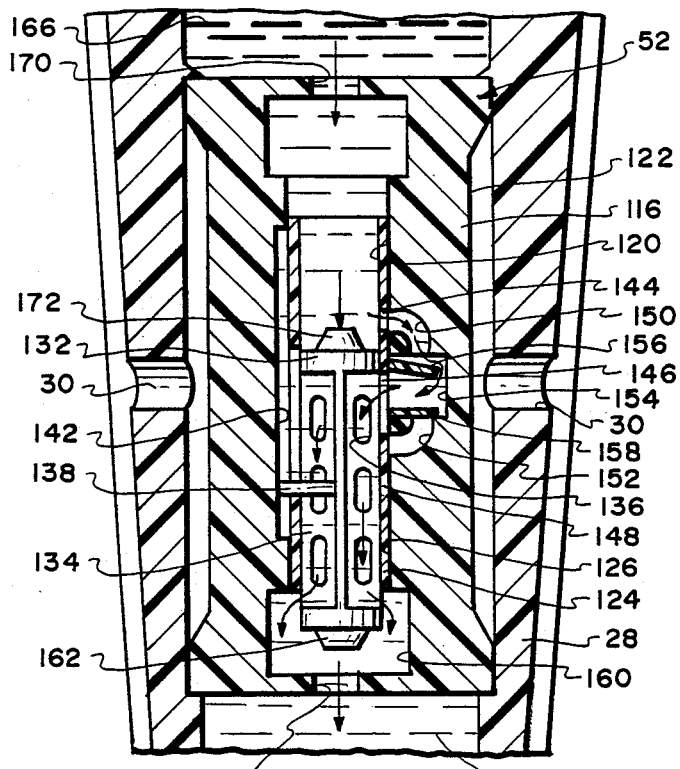
FIG. 22 is a view similar to FIG. 19 but showing the valve unit in the purging and injecting position.
Figure 23:
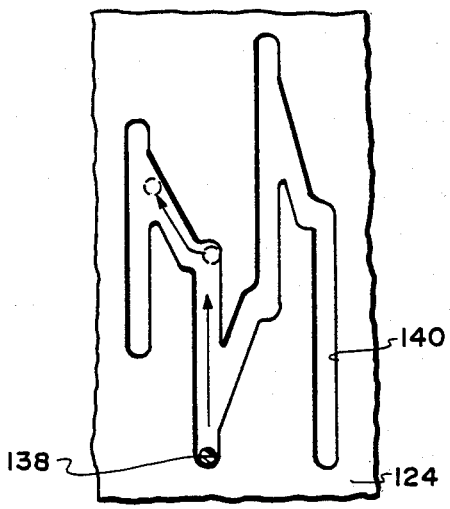
FIG. 23 is a view of the guide track of FIG. 17 showing the pin in its location in conjunction with this guide track to correspond to the position of FIG. 22.
Figure 24:
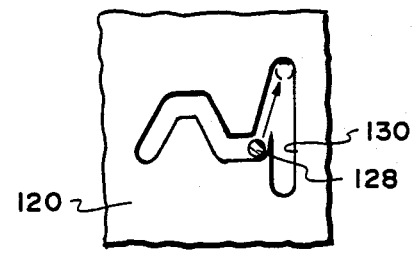
FIG. 24 is a view similar to FIG. 21 but showing its pin in its location again corresponding to the position of FIG. 22.

Let it now be assumed that someone does attempt to refill syringe 10 with a liquid 110. The attempting to refill will cause the refilling liquid to be conducted through hole 108 into passage 96. Passage 94 is closed by the valve spool 82 and with the only open avenue being for the liquid 110 to move against the valve spool 84. This causes valve spool 84 to move to an upward positionclosing of passage 100. The only thing that has occurred is that the flapper valve 70 is displaced slightly at one end due to the purging of any air and/or liquid that may be contained against the upper surface of the valve spool 84. No further liquid refilling will occur into the internal chamber 12. The position of the valve body 56 is now as shown in FIG. 13 of the drawings.

Any attempt to push the plunger 20 in the opposite direction will result in no conducting of fluid through any of the passages of the valve body 56.

It is considered to be a possibility that an enterprising individual could drill through the center of the valve unit 50 thereby possibly reuse the syringe 10. To avoid this, any drilling will open recesses 112 formed within the valve body 56. These open recesses 112 will connect with holes 30 or holes 48. Therefore, any attempt to fill the internal chamber 14 of the barrel 12 will result in the liquid being squirted out into the ambient through holes 30 and 48. The same would be true for any motion of the plunger 20 intending to move fluid from the internal chamber 14 into the passage 44 of the needle 46.

It is to be noted that the peripheral surface of the valve body 56 is contoured to form an annular enlarged recess 114. It is the function of this recess 114 to form, in essence, the chamber communicating with the holes 30. Therefore, any attempt to drill through the valve body 56, as previously mentioned, will surely cause one of the recesses 112 to be open to the recess 114 and will cause the liquid 110 to flow therethrough, through the holes 30 into the ambient.

The second embodiment 52 has a cylindrical valve body 116 which has formed therein a series of recesses 118. Recesses 118 are to function in the same manner as recesses 112 of the first embodiment 50. The valve body 116 includes a centrally disposed through opening 120. The exterior peripheral surface of the valve body 116 also forms an annular enlarged recess 122 which is for the same purpose as recess 114 of the first embodiment 50.

Within the through opening 120 is mounted a sleeve 124. This sleeve 124 includes a centrally disposed through opening 126. Mounted on the exterior surface of the sleeve 124 are a pair of pins 128. These pins 128 are located diametrically opposite each other. Each pin 128 connects with a guide track 130 formed within the surface of the through opening 120. It is to be understood that there will be a separate guide track (not shown) which similarly connects with the remaining pin 128 with this guide track being also identical in configuration to guide track 130. It is considered to be within the scope of this invention that there may be utilized only a single pin 128 and a single guide track 130.

Slidably mounted in a longitudinal manner within the through opening 126 is a spool 132. The spool 132 is defined with each end thereof by an enlarged annular head integrally connected together therebetween by a crossed plate arrangement 134. Within this crossed plate arrangement 134 is located a series of holes 136. Securely mounted to the crossed plate arrangement 134 is a pin 138. This pin 138 extends through a guide track 140 formed within the sleeve 124. The outer end of the pin 138 rests within a lineal slot 142 formed within the wall surface of the through opening 120.

Also formed within the sleeve 124 are holes 144, 146 and 148. These holes 144, 146 and 148 are capable of connecting with passages 150 and 152 as well as chamber 154 formed within valve body 116. Passages 150 and 152 connect with the chamber 154. Passage 150 is normally closed by a flexible flapper valve 156. In a similar manner the passage 152 is normally closed by a flexible flapper valve 158. Flapper valves 156 and 158 are mounted onto the wall of the chamber 154.

The operation of the embodiment 52 will now be described: Embodiment 52 will be in the position shown in FIG. 16 with the lower end of the spool 132 being located within chamber 160 of the valve body 116. The pin 138 is at the position of FIG. 17 with respect to the guide track 140. Pin 128 is in the position of FIG. 18 with respect to guide track 130. The sleeve 124 is located against the pin 138 and prevents the bottom end 162 of the spool 132 closing hole 164 of the valve body 116. As a result, liquid 166 is drawn during rearward movement of the plunger 20 through hole 164 of chamber 160, through plate holes 136, into chamber 154 and into groove 142. At this time no further movement of the liquid 166 is permitted. However, because of the pressure being applied against the upper end of the spool 132, the spool 132 is moved lineally with the pin 138 sliding within groove 142. This movement is shown within FIG. 19 of the drawings. Pin 138, in performing of this lineal movement, has moved within guide track 140 to the position shown in FIG. 20. As a result, the sleeve 124 has pivoted a few degrees relative to the spool 132. The liquid 166 is now capable of being conducted through passage 152, past flapper valve 158 into chamber 154, then past crossed plate arrangement 134, past the upper end of the spool 132 into chamber 168 formed within the valve body 116 and through hole 170 into the internal chamber 14 of the barrel 12. It is to be understood that the filling of the liquid 166 into the internal chamber 14 will continue as long as the plunger 20 continues to move in a rearward direction.

Let it now be assumed that filling has been completed and the plunger 20 is now moved in the reverse direction toward outlet opening 26. The spool 132 is moved lineally until finally will occupy the solid line position shown in FIG. 22. The pin 138 is also moved lineally as represented by the arrows within guide track 140 of FIG. 20 until the pin 138 comes into contact with slanted surface of the guide track 140 and further movement of the pin 138 will cause the sleeve 124 to pivot relative to the spool 132. The pin 128 is moved within its guide track 130 from the position shown in FIG. 21 to that of FIG. 24. The sleeve 124 has moved lineally within through opening 120 to the position of FIG. 22. At this time, liquid 166 is capable of being conducted through hole 170, chamber 168 into passage 150 past flapper valve 156 and into chamber 154. From chamber 154, the liquid 166 is conducted past crossed plate arrangement 134 and into chamber 160 and through hole 164 into the passage 44 of the needle 46. Once all of the liquid 166 contained within the internal chamber 14 has been injected into the patient and the tip 22 is located directly adjacent outlet opening 26 the injection of the liquid 166 no longer occurs.

Figure 25:
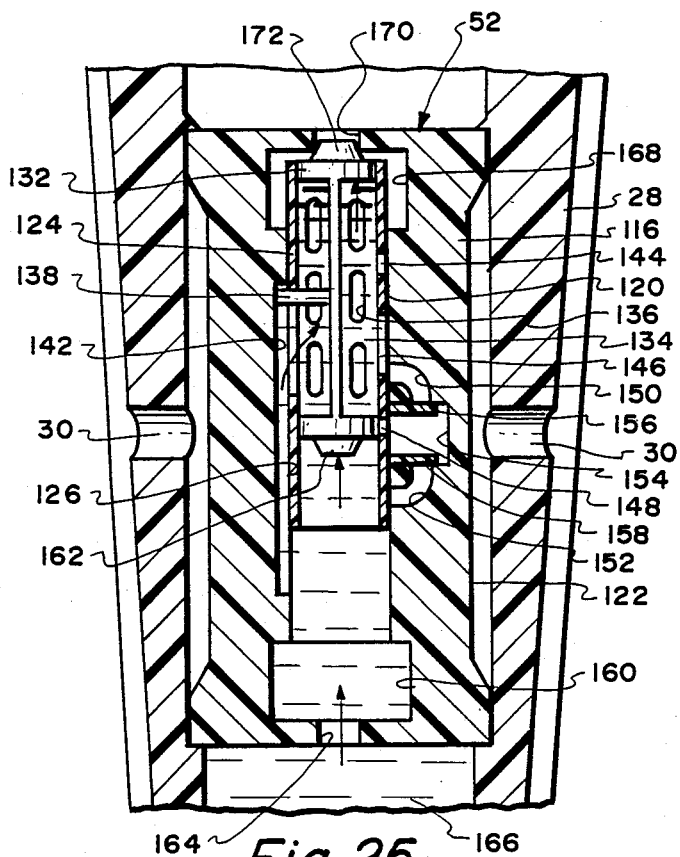
FIG. 25 is a view similar to FIG. 22 but showing the valve unit in the attempting to refill position.
Figure 27:
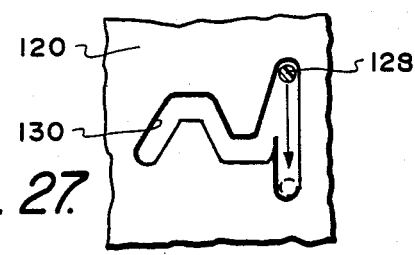
FIG. 27 is a view similar to FIG. 24 but showing its pin in its location corresponding to the position of FIG. 25.
Figure 28:
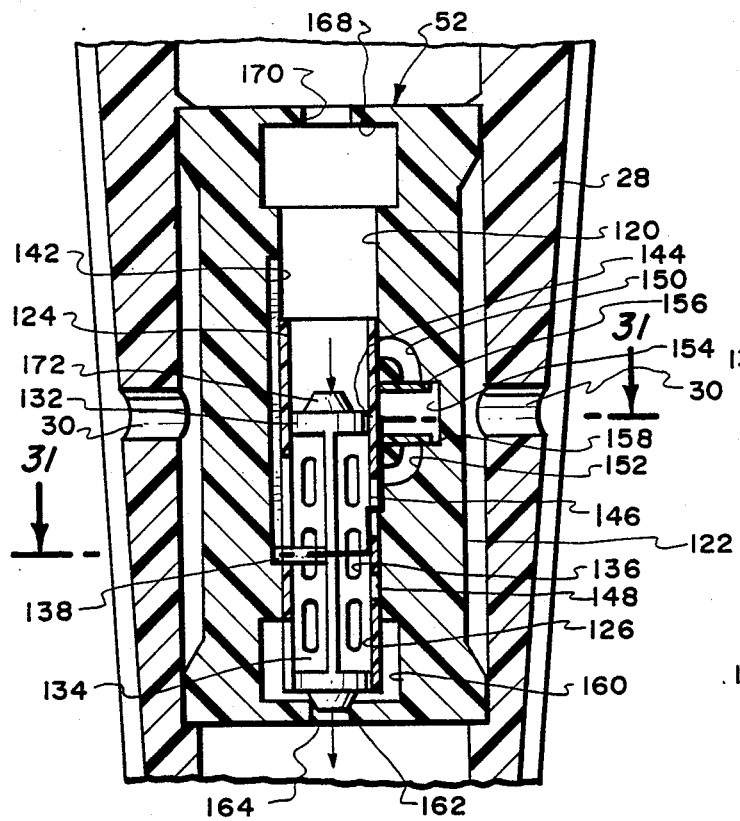
FIG. 28 is a view similar to FIG. 25 but showing the valve unit in the attempting to reinject position.

Let it now be assumed that the individual attempts to refill internal chamber 14. Pressure is again applied to the upper end of the spool 132 which causes the spool 132 to move into chamber 168 as is shown in FIG. 25 of the drawings. However, it is to be noted that the pin 138 occupies a somewhat lower position within the guide track 140 than what is occupied within the filling position shown in FIG. 19. As a result, the upper end of the spool 132 never disengages from the sleeve 124. However, the sleeve 124 has moved to within the chamber 168 which is permitted because the pin 128 has occupied a higher position within the guide track 130 as is shown in FIG. 27. Also, the sleeve 124 has again pivoted a few degrees caused by the movement of the pin 138 within the guide track 140. At this time, the upper end 172 of the valve spool 132 is moved against hole 170 and closes such. Therefore, movement of liquid 166 into the internal chamber 14 is prevented.

Figure 26:
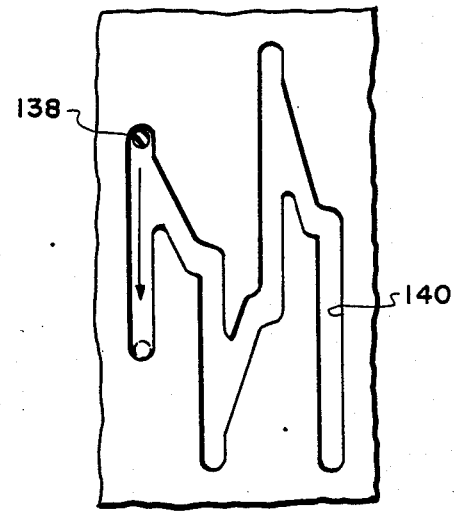
FIG. 26 is a view similar to FIG. 23 but showing the pin in its location corresponding to the position of FIG. 25.
Figure 29:
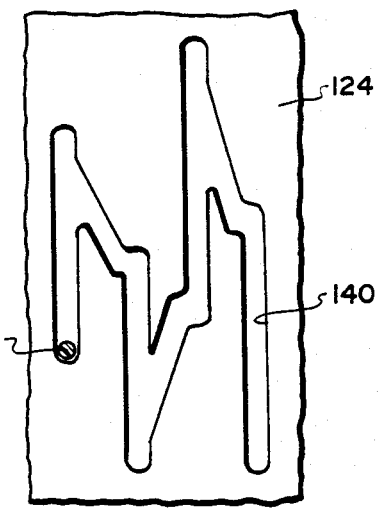
FIG. 29 is a view similar to FIG. 26 but showing its pin in its location corresponding to the position of FIG. 28.
Figure 30:
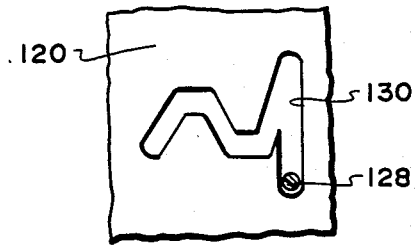
FIG. 30 is a view similar to FIG. 27 but showing its pin in its location corresponding to the position of FIG. 28.
Figure 31:
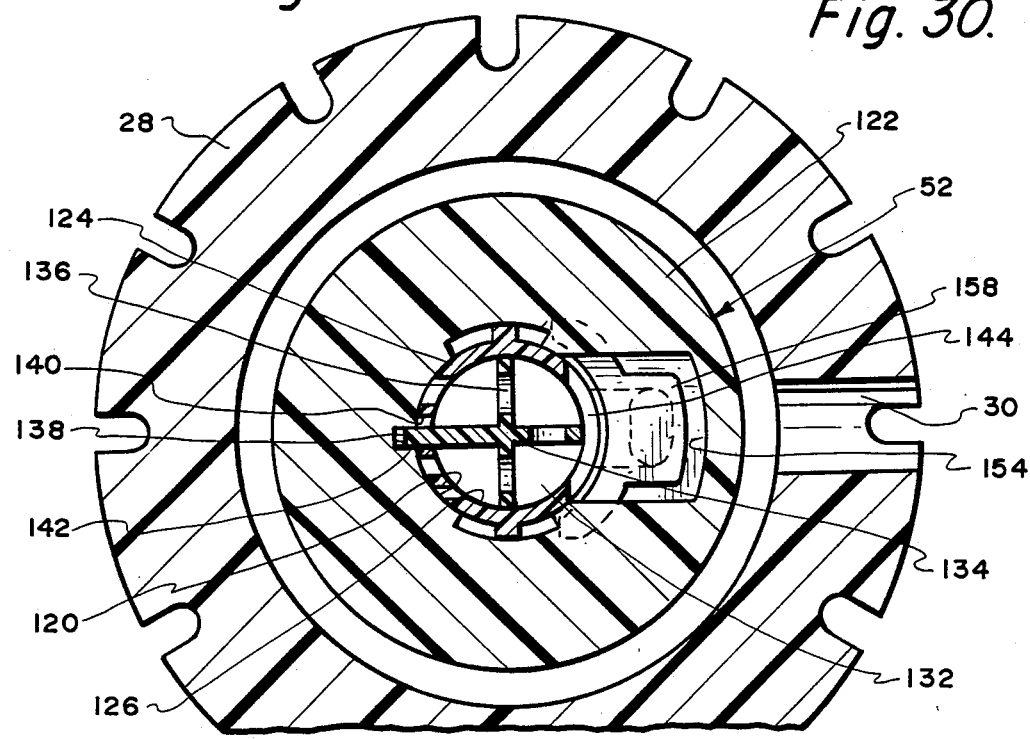
FIG. 31 is a transverse cross-sectional view through the second embodiment of valve unit of this invention taken along line 31—31 of FIG. 28.

If the user proceeds to push the plunger 20 in the inward or opposite direction, the pin 138 will move in a lineal manner within the guide track 140 from the position in FIG. 26 to the position in FIG. 29. In a similar manner, the pin 128 will also move in a lineal manner within its guide track 130 from the position shown in FIG. 27 to that within FIG. 30. The sleeve 124 and the spool 132 is moved from the position in FIG. 25 to the position in FIG. 28 with the bottom end 162 of the spool 132 coming against the hole 164 and closing such. Therefore, it is not possible to have any liquid 166 move into the passage 44 of the needle 46. Any movement of the plunger 20 in the opposite direction will merely cause the second embodiment 50 to be moved again to the position in FIG. 25.

Reference now is to be had to FIG. 53 in which there is shown a modified version guide track 176 which is incorporated within the wall of the sleeve 124. Modified version 176 is similar to the guide track 140 with the only difference having to do with the adding of an additional section which is composed of vertical portion 178, slanted portion 180, second vertical portion 182 and second slanted portion 184. When using the guide track 176, it is necessary that the guide track for the pin 128 be also modified to include an additional section composed of horizontal section 186, slanted portion 188, horizontal section 190 and slanted portion 192. These additional track sections provide for an additional withdrawing of the plunger 20 and an additional forward movement of the plunger 20 other than what was originally provided. The reason for this is that at times a medical practitioner, after insertion of the needle under the skin, wishes to withdraw the plunger to see if the needle has been located within a vein or artery and, if that practitioner sees that blood is now being withdrawn, the practitioner knows that he has so hit a vein or artery. By incorporating of these additional sections within the tracks 176 and 194, these additional two movements are provided.

Reference now is to be had to FIGS. 32 to 51 where there is shown the third embodiment of this invention. This third embodiment defines a valve body 196 which has an internal chamber 198. The upper end of internal chamber 198 connects to a hole 200 with the lower end of the internal chamber 198 connecting to a hole 202. Formed within the walls of the internal chamber 198 is a guide track 204. Connecting with this guide track 204 is a pin 206. Pin 206 is integrally formed on a disc 208. Disc 208 includes a centrally disposed opening 210. Also, included within the disc 208 are four in number of spaced apart holes 212. A pin 214 is closely mounted within hole 210. However, disc 208 is capable of being rotated relative to the pin 214.

The outer end of the pin 214 includes an enlarged head 216. Between the enlarged head 216 and the upper surface of the disc 208 is mounted a flexible plastic flapper valve 218. The flapper valve 218 includes a pair of spaced apart holes 221 which are in alignment with a specific pair of the holes 212 and will remain continuously in alignment with this specific pair of holes 212. The flapper valve 218 includes a central opening 219 through which the pin 214 is conducted with the enlarged head 216 resting against the upper surface of the flapper valve 218. The pin 214 is integrally mounted on a second disc 220. The disc 208 has the same size peripheral surface as disc 220. Disc 220 also includes four in number of spaced apart holes 222. The disc 208 rests on the disc 220. The lower surface of the disc 220 has a flexible plastic flapper valve 224 located thereagainst. This flapper valve 224 is held in position by enlarged head 226 which is integrally mounted on the disc 220. Enlarged head 226 engages with hole 228 formed within the flapper valve 224. The flapper valve 224 also includes a pair of spaced apart holes 230. One of the holes 230 is in alignment with one of the openings 222 with the other hole 230 being in continuous alignment with another one of the holes 222. A pin 232 is integrally formed and it protrudes from the side wall of the disc 220. This pin 232 is in continuous engagement with a slot 234 formed within the side wall of the internal chamber 198.

Figures 32, 35:
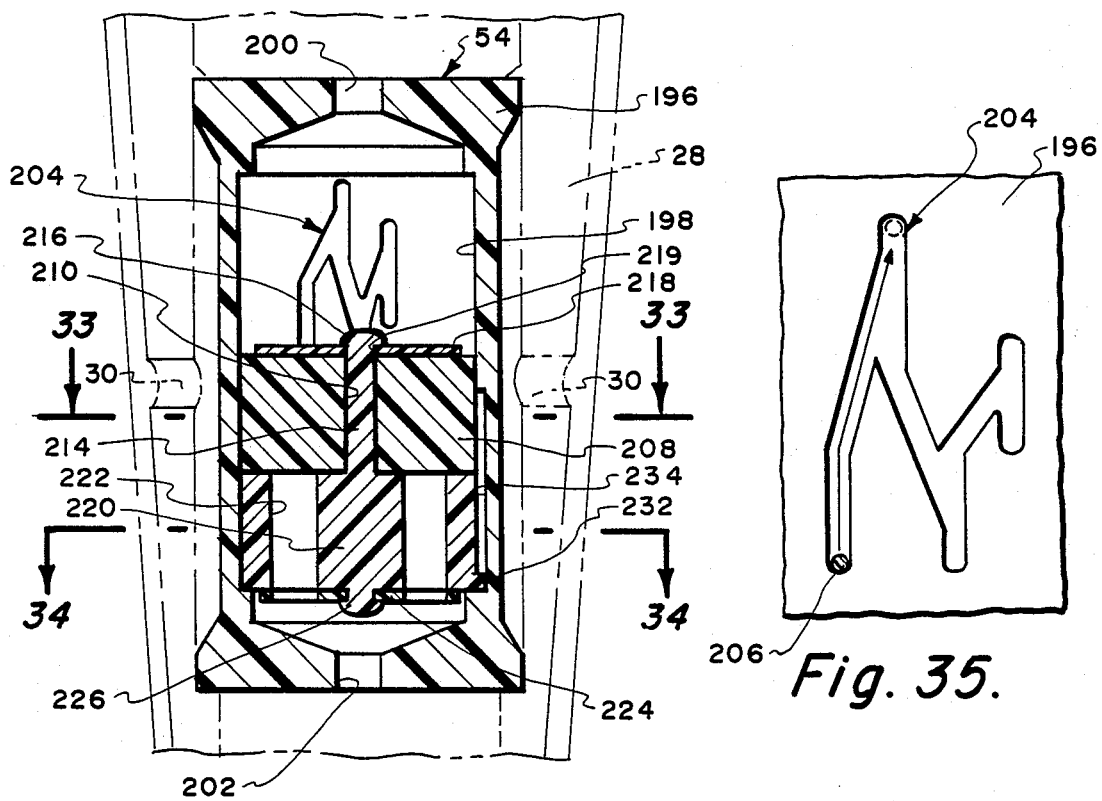
FIG. 32 is a longitudinal cross-sectional view through the third embodiment of valve unit included within this invention showing the valve unit in position in which it has been received by the medical practitioner.
FIG. 35 is a showing of a guide track included within the third embodiment of valve unit of this invention showing the location of a pin within the guide track to correspond to the position of FIG. 32.
Figures 33, 34:
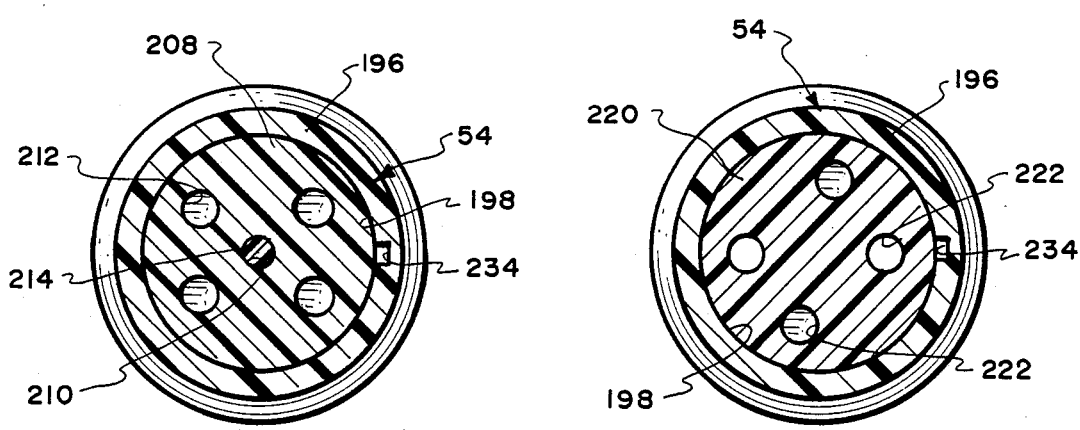
FIG. 33 is a transverse cross-sectional view taken along line 33—33 of FIG. 32.
FIG. 34 is a transverse cross-sectional view taken along line 34—34 of FIG. 32.
Figure 36:
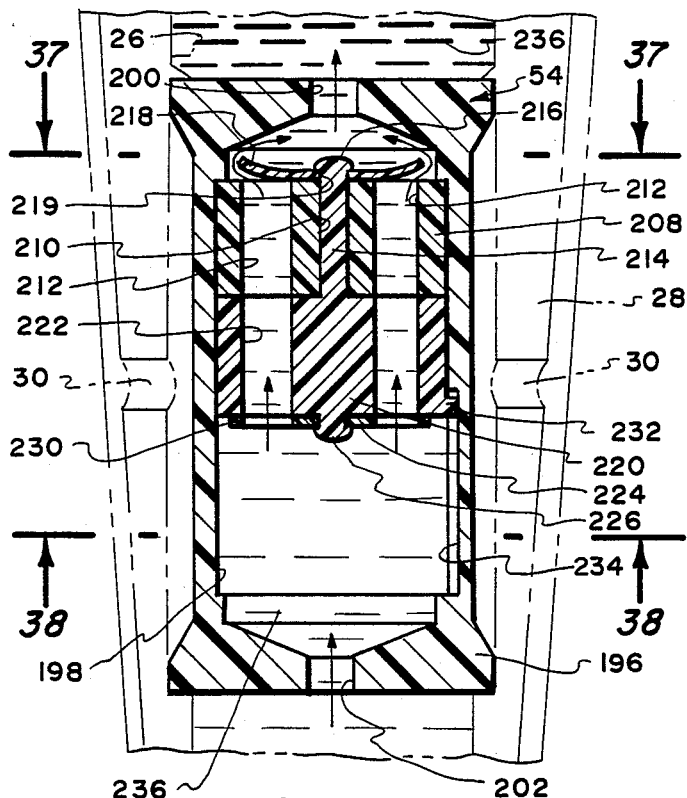
FIG. 36 is a view similar to FIG. 32 but showing the valve unit in the loading position.
Figure 39:
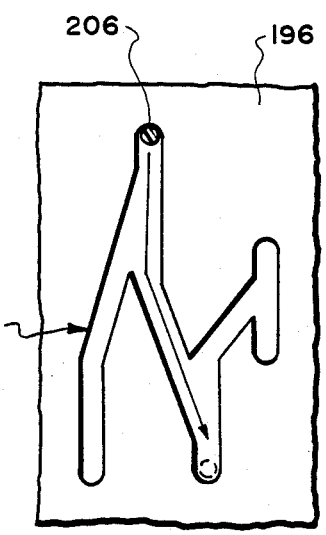
FIG. 39 is a view similar to FIG. 35 but showing the location of the pin within the guide track to correspond to the position of FIG. 36.
Figure 37:
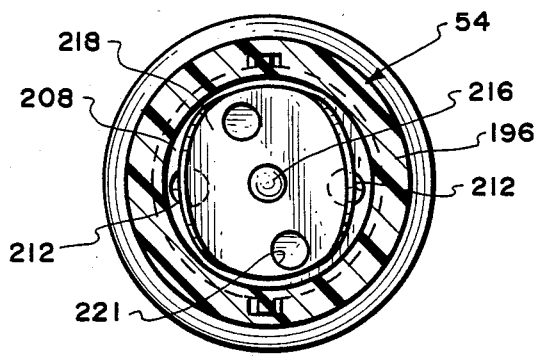
FIG. 37 is a transverse cross-sectional view taken along line 37—37 of FIG. 36.
Figure 38:
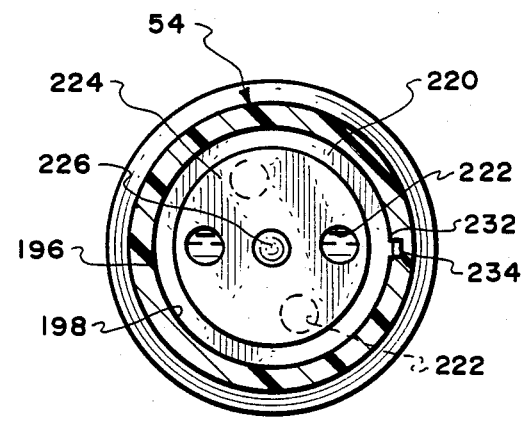
FIG. 38 is a transverse cross-sectional view taken along line 38—38 of FIG. 36.

The operation of the embodiment 54 of this invention is as follows: This embodiment 54 of valve unit is is in the position shown in FIG. 2 of the drawings when the syringe 10 is received by the medical practitioner. This position is shown in FIG. 32. During filling of the internal chamber 14 by the medicinal liquid 236, as the plunger 20 is moved rearwardly, the disc 208 and 220 move from the position shown in FIG. 32 to the position shown in FIG. 36. The pin 232 moves from the lower end of slot 234 to the upper end of the slot 234. It is the function of the pin 232 to prevent rotation of the disc 220. During this movement, the pin 206 rides within the left hand portion of the guide track 204 as observed in FIG. 35 until the position in FIG. 39 is obtained. During this movement, the disc 208 is caused to rotate sufficiently so that holes 212 will line up with holes 222. As a result, the medicinal liquid 236 is conducted through holes 202 into internal chamber 198 through holes 230 in the flapper valve 224 through holes 222 and 212 which causes then the flapper valve 218 to deflect permitting the liquid to pass through the hole 200 into the outlet opening 26 which connects with the internal chamber 14.

After filling of the internal chamber 14, flapper valve 218 is automatically moved to an at-rest position against the upper surface of the disc 208.

Figure 40:
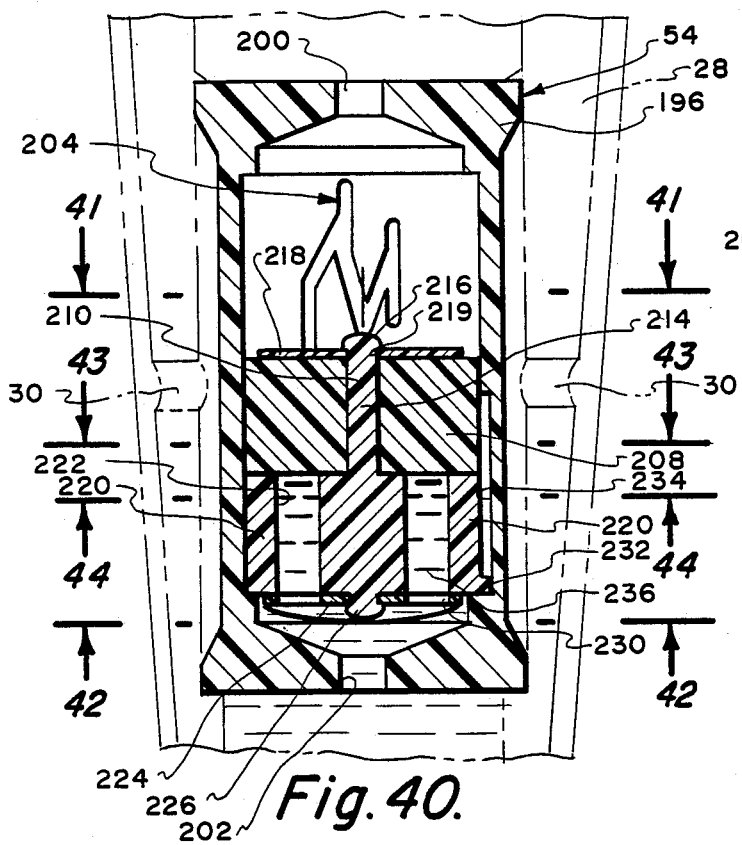
FIG. 40 is a view similar to FIG. 36 but showing the valve unit in the liquid injecting position.
Figure 45:
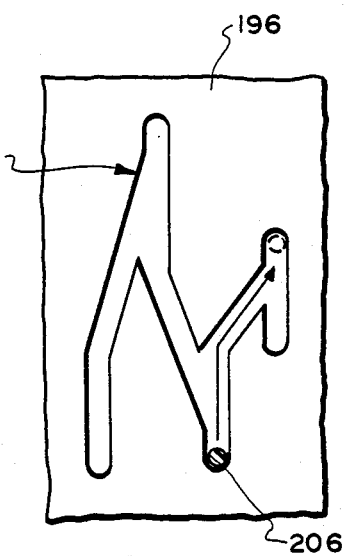
FIG. 45 is a view similar to FIG. 39 but showing the location of the pin in conjunction with the guide track corresponding to the position of FIG. 40.
Figure 41:
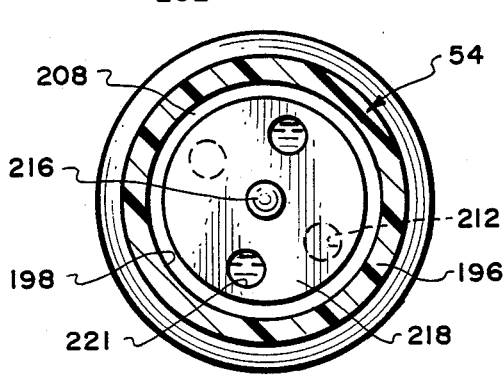
FIG. 41 is a transverse cross-sectional view taken along line 41—41 of FIG. 40.
Figure 43:
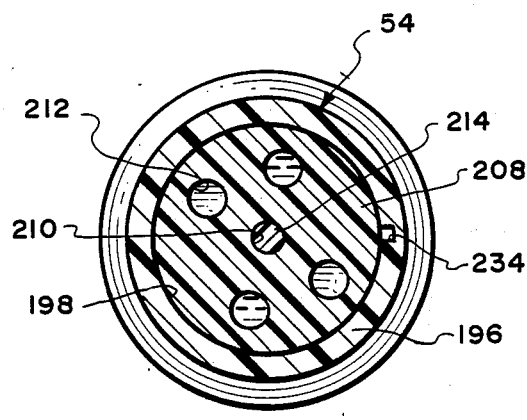
FIG. 43 is a transverse cross-sectional view taken along line 43—43 of FIG. 40.
Figure 42:
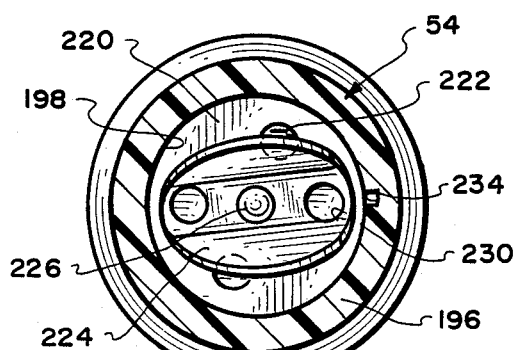
FIG. 42 is a transverse cross-sectional view taken along line 42—42 of FIG. 40.
Figure 44:
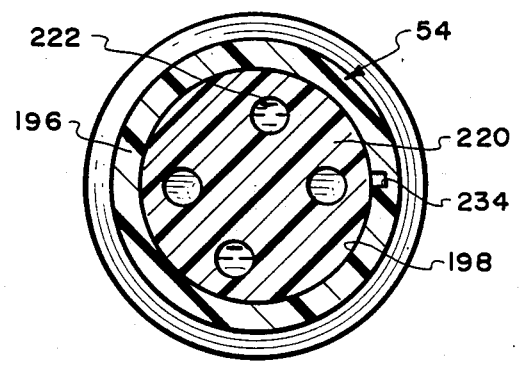
FIG. 44 is a transverse cross-sectional view taken along line 44—44 of FIG. 40.
Figure 46:
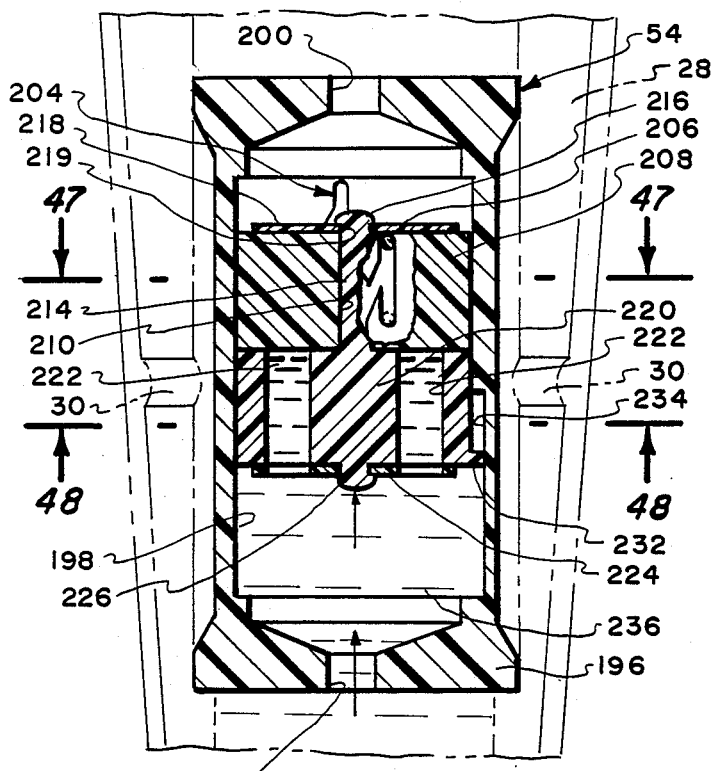
FIG. 46 is a view similar to FIG. 40 but showing the third embodiment of valve unit in an attempt to refill position.
Figure 49:
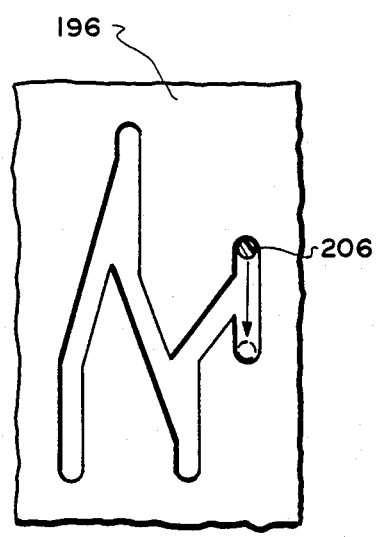
FIG. 49 is a view similar to FIG. 45 but showing the location of the pin corresponding to the position of FIG. 46.
Figure 47:
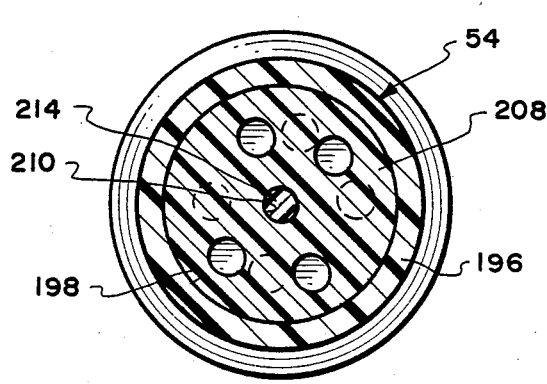
FIG. 47 is a transverse cross-sectional view taken along line 47—47 of FIG. 46.
Figure 50:
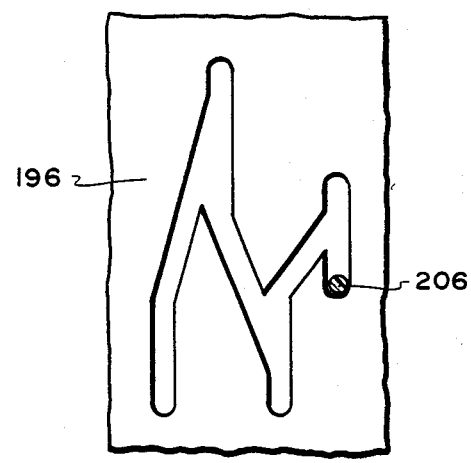
FIG. 50 is a view similar to FIG. 49 but showing the location of the pin in conjunction with the guide track in an attempt to inject position.
Figure 48:
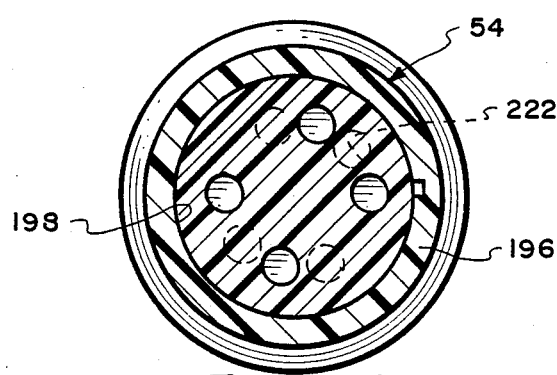
FIG. 48 is a transverse cross-sectional view taken along line 48—48 of FIG. 46.

The injection procedure occurs when the plunger 20 is moved toward outlet opening 26 which immediately causes both discs 208 and 220 to move to a lower position such as shown in FIG. 40. The pin 206 moves from the position in FIG. 39 to the position of FIG. 45 within the guide slot 204 which results in the discs 208 to again be rotated relative to disc 220. This rotation results in two of the holes 212 being aligned with the two holes 222 that are closed by the flapper valve 224.

As a result, the fluid is capable of being conducted through the holes 221, the corresponding pair of the aligned holes 212 and hence through the holes 222 that are aligned with this specific pair of holes. From there, the liquid 236 displaces flapper valve 224 and hence the liquid is then discharged into the outlet passage 44 of the needle 46.

After the injection is completed, the flapper valve 224 will automatically move back to its normal at-rest position against the disc 220 thereby closing the holes 222 through which the injection has occurred. If the user attempts to refill the internal chamber 14 of the barrel 12 of the syringe 10 and move the plunger 20 to a rearwardly displaced position, the pin 206 is moved from the position shown in FIG. 45 to the position in FIG. 49. This in turn rotates the disc 208 sufficiently so that none of the holes 212 align with any of the holes 222. The disc 208 is now maintained in that position relative to disc 220 with the result that the liquid 236 is not capable of being moved through the valve unit embodiment 54 in either direction. Any attempt to again drill out the valve unit embodiment 54 will result in holes 30 being exposed to cause dispensing of the liquid therethrough when any attempt is made to inject liquid by the use of the syringe 10.

Referring particularly to FIG. 52, there is shown a guide track 238 which is different from guide track 204 in that there is an additional track section composed of vertical track 240, slanted section 242, vertical section 244 and slanted section 246. This additional section provides for again an additional withdrawing movement to ascertain whether the user has located the needle 46 within a vein or artery and then the additional injection movement. It is to be understood that the guide track 238 could be used instead of the guide track 204.

What is claimed is:

1. A single use syringe comprising:
   an elongated barrel having an internal chamber, said barrel having an outlet opening at one end and an inlet opening at the opposite end, said outlet opening being part of an outlet chamber;

a plunger movably mounted within said internal chamber, a portion of said plunger extending exteriorly of said inlet opening, said plunger terminating in an inner end defining a tip, said tip being located within said internal chamber in a snug fitting manner closing said inner end from the ambient;

a needle assembly attached to said barrel at said outlet opening, said needle assembly having an interior chamber, said interior chamber being part of said outlet chamber, the improvement comprising:

a valve system mounted within said outlet chamber, said valve system including a valve body, said valve system including a passage arrangement formed within said valve body, said passage arrangement permitting flow of liquid from said internal chamber to said needle assembly only a predetermined number of times, upon said predetermined number of times having occurred said passage arrangement closes preventing flow of liquid from said internal chamber to said needle assembly; and said valve system including at least one movable member, said member being movable from an open position to a closed position, said member being moved solely by liquid pressure as liquid is drawn into said internal chamber and as liquid is expelled from said internal chamber.

2. The single use syringe as defined in claim 1 wherein:
said valve system comprising two in number separate valve units, one of said valve units being located within said outlet opening and the other said valve unit being located within said interior chamber.

3. The single use syringe as defined in claim 1 wherein:
said predetermined number of times comprising a single time.

4. The single use syringe as defined in claim 1 wherein:
said predetermined number of times comprising two in number of times.

5. The single use syringe as defined in claim 1 wherein:
said valve system comprising a plurality of valve spools being mounted within said valve body and associated with said passage arrangement.

6. The single use syringe as defined in claim 1 wherein:
the movement of said member can only be in a prescribed sequence and cannot be reversed.

7. The single use syringe as defined in claim 1 wherein:
the movement of said member can only be on a prescribed path.

8. A single use syringe comprising:
an elongated barrel having an internal chamber, said barrel having an outlet opening at one end and an inlet opening at the opposite end, said outlet opening being part of an outlet chamber;

a plunger movably mounted within said internal chamber, a portion of said plunger extending exteriorly of said inlet opening, said plunger terminating in an inner end defining a tip, said tip being located within said internal chamber in a snug fitting manner closing said inner end from the ambient;

a needle assembly attached to said barrel at said outlet opening, said needle assembly having an interior chamber, said interior chamber being part of said outlet chamber, the improvement comprising:

a valve system mounted within said outlet chamber, said valve system including a valve body, said valve system including a passage arrangement formed within said valve body, said passage arrangement permitting flow of liquid from said internal chamber to said needle assembly only a predetermined number of times, upon said predetermined number of times having occurred said passage arrangement closes preventing flow of liquid from said internal chamber to said needle assembly; and said needle assembly including a needle housing, said valve system including a valve unit, said valve unit being mounted within said needle housing, said needle housing having at least one hole formed through the side wall of said needle housing connecting with said valve unit, whereby upon any effort being expended to remove said valve unit from said needle housing will result in the liquid from said barrel being expelled into the ambient through said hole rather than solely through said needle assembly thereby preventing operation of said syringe in the normal manner.

9. A single use syringe comprising:
an elongated barrel having an internal chamber, said barrel having an outlet opening at one end and an inlet opening at the opposite end, said outlet opening being part of an outlet chamber;

a plunger movably mounted within said internal chamber, a portion of said plunger extending exteriorly of said inlet opening, said plunger terminating in an inner end defining a tip, said tip being located within said internal chamber in a snug fitting manner closing said inner end from the ambient;

a needle assembly attached to said barrel at said outlet opening, said needle assembly having an interior chamber, said interior chamber being part of said outlet chamber, the improvement comprising:

a valve system mounted within said outlet chamber, said valve system including a valve body, said valve system including a passage arrangement formed within said valve body, said passage arrangement permitting flow of liquid from said internal chamber to said needle assembly only a predetermined number of times, upon said predetermined number of times having occurred said passage arrangement closes preventing flow of liquid from said internal chamber to said needle assembly; and said valve body including a lineally movable valve spool, said valve spool connecting with said passage arrangement, said valve spool functioning to open and close said passage arrangement.

10. The single use syringe as defined in claim 9 wherein:
said valve spool being pivotally mounted relative to said valve body, the pivot movement of said valve spool being determined by a guide track located between said valve spool and said valve body.

11. A single use syringe comprising:
an elongated barrel having an internal chamber, said barrel having an outlet opening at one end and an inlet opening at the opposite end, said outlet opening being part of an outlet chamber;

a plunger movably mounted within said internal chamber, a portion of said plunger extending exteriorly of said inlet opening, said plunger terminating in an inner end defining a tip, said tip being located within said internal chamber in a snug fitting manner closing said inner end from the ambient;

a needle assembly attached to said barrel at said outlet opening, said needle assembly having an interior chamber, said interior chamber being part of said outlet chamber, the improvement comprising:

a valve system mounted within said outlet chamber, said valve system including a valve body, said valve system including a passage arrangement formed within said valve body, said passage arrangement permitting flow of liquid from said internal chamber to said needle assembly only a predetermined number of times, upon said predetermined number of times having occurred said passage arrangement closes preventing flow of liquid from said internal chamber to said needle assembly; and said valve system including a valve spool being mounted within a spool sleeve, said sleeve being mounted within said valve body, said valve spool being pivotable relative to said spool sleeve, said valve spool being lineally movable relative to said spool sleeve, said spool sleeve being lineally movable within said valve body.

12. A single use syringe comprising:

an elongated barrel having an internal chamber, said barrel having an outlet opening at one end and an inlet opening at the opposite end, said outlet opening being part of an outlet chamber;

a plunger movably mounted within said internal chamber, a portion of said plunger extending exteriorly of said inlet opening, said plunger terminating in an inner end defining a tip, said tip being located within said internal chamber in a snug fitting manner closing said inner end from the ambient;

a needle assembly attached to said barrel at said outlet opening, said needle assembly having an interior chamber, said interior chamber being part of said outlet chamber, the improvement comprising:

a valve system mounted within said outlet chamber, said valve system including a valve body, said valve system including a passage arrangement formed within said valve body, said passage arrangement permitting flow of liquid from said internal chamber to said needle assembly only a predetermined number of times, upon said predetermined number of times having occurred said passage arrangement closes preventing flow of liquid from said internal chamber to said needle assembly; and said valve system including a stacked series of discs, at least one said disc being pivotable relative to another said disc, each said disc including an opening arrangement, said opening arrangement to connect with said passage arrangement to conduct liquid from said barrel to said needle assembly.

13. The single use syringe as defined in claim 12 wherein:

the movement of said disc being determined by a guide track, said valve body having said guide track formed therein.

14. The single use syringe comprising:

an elongated barrel having an internal chamber, said barrel having an outlet opening at one end and an inlet opening at the opposite end, both said outlet opening and said inlet opening connecting with said internal chamber;

a plunger movable mounted within said internal chamber, a portion of said plunger extending exteriorly of said inlet opening, said plunger terminating in an inner end defining a tip, said tip located in a snug fitting manner within said internal chamber;

a needle attached to said barrel at said outlet opening, said needle having a through opening, movement of said plunger is capable of causing the liquid to be dispensed from internal chamber through said through opening, the improvement comprising:

a valve apparatus mounted within said internal chamber, said valve apparatus including a valve body, a passage arrangement formed in said valve body, said passage arrangement permitting flow of a liquid from said internal chamber into said through opening, a member movably mounted on said valve body, said member being moved solely by the pressure of the liquid as such enters said internal chamber and is discharged therefrom, said member being locatable in a first position and a second position, said first position permitting flow of liquid through said through operating, said second position preventing flow of liquid through said through opening.

15. The single use syringe as defined in claim 14 wherein:

said member being movable along a specifically defined path, as said member is moved along said path said member occupies a different position with reversing movement of said member not possible.

16. The single use syringe as defined in claim 15 wherein:

said member comprising a disc, said disc being pivotable relative to said valve body, said disc including an opening arrangement, said opening arrangement connecting with said passage arrangement when said disc is in said first position.

* * * * *